United States Patent [19]

Casale et al.

[11] Patent Number: 5,714,634
[45] Date of Patent: *Feb. 3, 1998

[54] PROCESS FOR STORAGE AND TRANSPORT OF TOLUENEDIAMINE

[75] Inventors: Andrew James Casale, New Tripoli; Richard Van Court Carr, Allentown, both of Pa.

[73] Assignee: Air Products and Chemicals, Inc., Allentown, Pa.

[*] Notice: The term of this patent shall not extend beyond the expiration date of Pat. No. 5,449,832.

[21] Appl. No.: 671,559

[22] Filed: Jun. 25, 1996

[51] Int. Cl.$^6$ .............................. C07C 209/36; B01D 3/00
[52] U.S. Cl. ........................ 564/422; 564/305; 203/12; 203/13
[58] Field of Search ......................... 564/422, 305; 203/12, 13

[56] References Cited

U.S. PATENT DOCUMENTS 5,449,832   9/1995   Carr et al. .................. 564/422

Primary Examiner—José G. Dees
Assistant Examiner—Barbara Badio
Attorney, Agent, or Firm—Russell L. Brewer; William F. Marsh

[57] ABSTRACT

This invention relates to an improved process for storing and transporting toluenediamine, particularly for long term storage or storage in large containers, e.g., shipboard containers. The improvement in the process resides in substantially reducing the melting or freezing point of anhydrous toluenediamine obtained by the fractional distillation of a reaction product generated by the hydrogenation of dinitrotoluene. Such melting point reduction is accomplished by maintaining a water concentration in the toluenediamine in an amount of from 5 to 15% by weight under molten conditions for storage and transport. Preferably the level of water maintained in the toluenediamine is from about 7 to 10% by weight.

4 Claims, No Drawings

PROCESS FOR STORAGE AND TRANSPORT OF TOLUENEDIAMINE

TECHNICAL FIELD OF THE INVENTION

The invention relates to an improved process for preparing toluenediamine mixture comprising largely meta-toluenediamines for storage and transport under liquid phase conditions.

BACKGROUND OF THE INVENTION

Toluenediamine is made commercially by hydrogenating a feedstock consisting essentially of dinitrotoluene isomers. One commercial method for producing dinitrotoluene is by a process referred to as mixed acid nitration. In such process toluene is contacted with nitric acid in the presence of sulfuric acid under conditions for producing a reaction product containing primarily the meta-dinitrotoluenes, viz., 2,4- and 2,6-dinitrotoluene (65–80% 2,4- and 20–35% 2,6-). The meta-dinitrotoluene fraction typically comprises at least 90% of the reaction product, with a small fraction comprising the ortho isomers. The dinitrotoluenes in the reaction product are recovered and then contacted with hydrogen in the presence of a hydrogenation catalyst, e.g., Raney nickel. On completion of the hydrogenation, the reaction product containing predominately the corresponding meta-toluenediamines is distilled under reduced pressure and elevated temperature (360° to 390° F.) and any lights, water, toluidine, ortho-toluenediamine and byproducts removed. Following distillation, the meta-toluenediamines are recovered from the bottom of the column at a temperature of about 390° F. and passed to a product cooler where the temperature is reduced to about 230°–250° F. and the pressure elevated to atmospheric. The resulting meta-toluenediamine isomer mixture is sent to storage.

Toluenediamine is a high melting aromatic diamine having a melting point of about 105° C. or 220° F. Because of its high melting point, storage and transport becomes difficult, particularly in large containers such as encountered on ships. If the meta-toluenediamine isomer mixture is allowed to convert to a solid in such large containers, the toluenediamine mixture may undergo degradation on remelting due to poor heat transfer. Not only is there a problem with stability, there is the problem of remelting a large solid block because of such poor heat transfer. Attempts have been made to granulate toluenediamine for remelting, but such attempts also have remained unacceptable because of poor heat transfer between the solid granules. The meta-toluenediamine containing isomer mixture then is typically stored in small vessels and transported by truck or transport vehicles equipped to maintain toluenediamine at a temperature in excess of its melting point.

Long term storage and transport in large containers such as present in ocean-going vessels is extremely difficult because of equipment requirements necessary to maintain the stored toluenediamine at a temperature above its melting point. Aside from the equipment requirements for maintaining the toluenediamine at a temperature above its melting point, there is the operational energy cost component associated with the storage and transport process.

U.S. Pat. No. 5,449,832 addresses the problem of shipping toluenediamine in large containers by adding water in an amount of from 5 to 15% by weight to high temperature toluenediamine. The temperature for addition of water is between 200° to 250° C.

SUMMARY OF THE INVENTION

This invention relates to an improved process for producing a toluenediamine mixture containing a large fraction of meta-toluenediamines for storage and transportation, particularly storage in large containers, e.g., shipboard containers. A basic process for producing toluenediamine comprises effecting dinitration of toluene, as stated in the background of the invention, and producing a reaction product containing a large fraction, e.g., >90%, by weight of the meta-dinitrotoluenes (2,4- and 2,6-dinitrotoluene) hydrogenating the reaction product containing a large fraction of meta-dinitrotoluenes under conditions for forming a hydrogenated toluenediamine product containing a large fraction of meta-toluenediamine, distilling the hydrogenated reaction product at reduced pressure and elevated temperature, cooling the resulting distillation product and recovering the distillation product for storage or shipment. The improvement in this process resides in substantially reducing the melting point of the distillation product containing a large fraction of the meta-toluenediamines by only partially removing the water in the molten toluenediamine reaction product during distillation. The water content in the molten toluenediamine is adjusted within a range of from 5 to 15% by weight of the molten distillation product. Preferably the level of water within the molten toluenediamine is adjusted to a range from about 7 to 10% by weight. If water is added to the molten toluenediamine to bring the water content within the desired range, one controls the temperature of the resultant toluenediamine-water mixture such that the final temperature of the toluenediamine-water mixture is at or below the boiling point of water.

There are significant advantages associated with the process of this invention and they include:

- an ability to substantially reduce the freezing point of meta-toluenediamines by controlling the water content within the toluenediamine reaction product containing a large fraction of meta-toluenediamines to permit storage and transport, particularly transport on ocean-going vessels;
- an ability to reduce energy costs associated with maintaining toluenediamine in liquid phase conditions for long term storage or extended transport;
- an ability to convert meta-toluenediamines to low melting solids without effecting discoloration, substantial byproduct formation and stability during storage; and,
- an ability to effect only partial removal of water from a meta-toluenediamine containing mixture during distillation thus saving energy costs.

DETAILED DESCRIPTION OF THE INVENTION

Toluenediamines are typically produced by the hydrogenation of dinitrotoluene, dinitrotoluene being produced by the mixed acid nitration of toluene. The reaction product obtained from the hydrogenation of dinitrotoluene is fractionally distilled, under vacuum, removing light (highly volatile) material such as deaminated product, ammonia and residual water which is produced during the reaction. Typically, complete distillation is effected which removes the byproducts and residual water from the reaction product thereby generating an anhydrous product containing a large fraction of meta-toluenediamines, viz. 2,4- and 2,6-toluenediamine having minimal contaminants therein. Contaminants primarily include the ortho-toluenediamines. The temperature of the resultant molten meta-toluenediamine mixture which is recovered at the bottom of the distillation column is generally from about 380° to 400° F.

It has been found that one can render the meta-toluenediamines in the bottoms fraction suitable for long term storage and suitable for ship transport without adversely affecting the product during such storage and transport. This is accomplished by reducing the melting point of the meta-toluenediamines from about 200° to 250° F. to about 145° to 165° F. through the control of water in the molten toluenediamine.

One of the significant advantages of this process is that the water in the feedstock toluenediamine is only partially removed rather than completely removed as done in the past to generate a toluenediamine fraction containing predominately 2,4- and 2,6-toluenediamine. By removing only a partial fraction of the water during fractionation, one may cool the resultant molten fraction to the storage temperature and stored without addition of water. Alternatively, one may add a smaller fraction of water than would have been required had there been complete distillation. Partial removal of the feedstock water reduces energy costs associated with distillation while at the same time provides a toluenediamine product which is suited for storage in large containers and/or shipment in large containers at reduced temperature.

If water should be added to the partially distilled feedstock hot, (160°–190° F.) water only reduces the temperature of the toluenediamine product containing meta-toluenediamine slightly from the desired 220° to 250° F. If the water is at 80°–90° F. the temperature is reduced slightly more but typically the temperature is reduced to about 200°–225° F. In either case, the resultant final temperature level provides sufficient internal heat for an extended period of time and an external heat source may not be required. In other words, the final temperature of the product toluenediamine after partial distillation is well above the freezing point of the product toluenediamine mixture. Thus, one is afforded substantial residual heat in the product for maintaining liquid phase conditions for extended periods of time.

Water concentrations greater than about 15% can be utilized to reduce the toluenediamine freezing point to a lower temperature, although such reduction in freezing point generally is small and does not result in energy efficiency. Water, because of its high heat capacity not only reduces the temperature of the toluenediamine, energy costs associated with the subsequent removal of the water through distillation are increased.

To recover the molten toluenediamine product from storage and prepare for final use, the product is distilled further to remove residual water and deleterious ortho-toluenediamine isomers. Complete distillation in prior cases eliminated the need for extensive distillation at the customers suited for use as a precursor to toluenediisocyanate.

The following example is intended to illustrate a preferred embodiment and is not intended to restrict the scope thereof.

EXAMPLE 1

Freezing Point Measurements

A series of tests were carried out for the purpose of determining the influence of water on the freezing point and stability of anhydrous toluenediamine in the presence of water. As determined herein, the freezing point is the temperature at which crystallization begins and does not refer to the temperature at which the entire mass of toluenediamine is a solid.

Molten toluene was mixed with various levels of water and cooled at a slow rate. Temperatures were taken of the mass as a function of time. When the temperature held constant for a period of about 15 minutes, the freezing point was noted. The table sets forth the results.

| Freezing Point | | | | |
|---|---|---|---|---|
| Temperature °F. | 170 | 165 | 160 | 150 |
| Weight % Water | 3.4 | 4.9 | 5.6 | 10.1 |

The toluenediamine-solute mixtures were found to be stable for a period of 30 days at 185° F. and without phase separation.

EXAMPLE 2

Process to recover 93% by weight crude TDA Containing 7% water from TDA reactor effluents A TDA reactor effluent containing approximately 60 weight % TDA and 40 weight % Water at a temperature of 295° F. and a pressure of 70 psia is treated in a manner so as to produce a final product suited for transport in large shipboard containers. The TDA reactor effluent is fed to a midpoint of a water removal distillation column operating at an overhead pressure of 15 psia and an overall column pressure drop of 1 psi. The column consists of 8 operating theoretical stages, 6 above the feed point and 2 below the feed point. This column permits operation in such a fashion so as to remove the water to such a degree that the bottoms stream contains 93 weight % Crude TDA and 7 weight % Water and an overheads wastewater stream containing not more than 300 parts per million by weight of combined TDA Isomers.

For a plant cable of generating 100 Million Lbs/Yr. of wet crude TDA, 21532 lbs/hr of a 60 weight % Crude TDA/40 weight % Water mixture are fed to the Water Removal Column.. The water removal column condenser temperature is 212.6° F. and the reboiler temperature is 249.1° F. A column reflux ratio of 0.038 maintains the overhead crude TDA content at 300 ppm by weight and a column boilup ratio of 2.21 maintains the water content of the bottoms at 7 weight %. The column reboiler and condenser duties are 6.61 Million BTU/hr and 7.78 Million BTU/hr, respectively. The resulting crude TDA consists of:

76.16 weight % 2,4-TDA
18.51 weight % 2,6-TDA
1.46 weight % 2,3-TDA
2.29 weight % 3,4-TDA
0.69 weight % 2,5-TDA
0.70 weight % heavy by-products such as TDA Tars
0.19 weight % light by-products such as toluidines, aniline.

The product is well suited for shipment in shipboard containers primarily because of the reduced freezing point of the TDA and high (249° F. temperature.

What is claimed is:

1. In a process for preparing a toluenediamine product containing a large fraction of 2,4- and 2,6-toluenediamine for storage and/or transportation in large containers which comprises the steps of effecting dinitration of toluene by the mixed acid method and producing a reaction product containing a large fraction of 2,4- and 2,6-dinitrotoluene, hydrogenating the reaction product containing 2,4- and 2,6-dinitrotoluene under conditions for forming a hydrogenated reaction product containing 2,4- and 2,6-toluenediamine, distilling water and contaminants from the hydrogenated reaction product at reduced pressure and elevated temperature, cooling the resultant distillation product and recovering the distillation product thereby generating a toluenediamine product for storage or shipment, the improvement which comprises:

only partially removing the water in the hydrogenated reaction product during distillation;

adjusting the water content in the distillation product containing a large fraction of 2,4- and 2,6-toluenediamine in an amount of from 5 to 15% by weight of the distillation product thereby generating a molten toluenediamine-water mixture; and controlling the temperature of the resultant toluenediamine-water mixture such that the final temperature of the toluenediamine-water mixture is at or below the boiling point of water.

2. The process of claim 1 wherein the water is added at a level of from about 7 to 10% by weight.

3. The process of claim 1 wherein the large fraction of 2,4- and 2,6-toluenediamine comprises from about 65–80% 2,4-toluenediamine and from about 20–35% 2,6-toluenediamine.

4. In a process for producing a meta-toluenediamine mixture wherein toluene is contacted with nitric acid in the presence of sulfuric acid under conditions for producing a reaction product containing primarily a 2,4- and 2,6-dinitrotoluene isomer mixture, the dinitrotoluene recovered and then contacted with hydrogen in the presence of a hydrogenation catalyst, the resulting reaction product containing 2,4- and 2,6-toluenediamine formed into a molten toluenediamine mixture, distilled in a column under reduced pressure and elevated temperature to remove any lights, water, toluidine, ortho-toluenediamine and byproducts, the substantially anhydrous meta-toluenediamine isomer mixture recovered from the bottom of the column and passed to a product cooler where the temperature is reduced to about 200°–250° F. and the pressure elevated to at least atmospheric, the improvement for preparing the resulting meta-toluenediamine isomer mixture for storage and/or transport which comprises:

partially removing the water in the molten toluenediamine mixture during distillation, adjusting the water content in the molten toluenediamine, in an amount of from 5 to 15% by weight of the molten toluenediamine, and controlling the temperature of the resultant toluenediamine-water mixture such that the final temperature of the toluenediamine-water mixture is at or below the boiling point of water.

* * * * *